(12) United States Patent
Sivovolenko et al.

(10) Patent No.: US 11,226,292 B2
(45) Date of Patent: Jan. 18, 2022

(54) METHOD FOR ANALYSING A GEMSTONE

(71) Applicant: OctoNus Finland OY, Tampere (FI)

(72) Inventors: Sergey Borisovich Sivovolenko, Ylöjärvi (FI); Janak Mistry, Tampere (FI); Roman Sergeevich Serov, Tampere (FI)

(73) Assignee: OCTONUS FINLAND OY, Tampere (FI)

( * ) Notice: Subject to any disclaimer, the term of this patent is extended or adjusted under 35 U.S.C. 154(b) by 0 days.

(21) Appl. No.: 16/606,212

(22) PCT Filed: Apr. 13, 2018

(86) PCT No.: PCT/EP2018/059493
§ 371 (c)(1),
(2) Date: Oct. 17, 2019

(87) PCT Pub. No.: WO2018/192842
PCT Pub. Date: Oct. 25, 2018

(65) Prior Publication Data
US 2020/0371042 A1 Nov. 26, 2020

(30) Foreign Application Priority Data
Apr. 19, 2017 (BE) .................................. 2017/5270

(51) Int. Cl.
*G01N 21/87* (2006.01)
*G01N 21/03* (2006.01)
(Continued)

(52) U.S. Cl.
CPC ............. *G01N 21/87* (2013.01); *G01N 21/03* (2013.01); *G01N 21/41* (2013.01); *G01N 33/381* (2013.01); *G01N 2201/0231* (2013.01)

(58) Field of Classification Search
CPC ...... G01N 21/87; G01N 21/64; G01N 33/381; G01N 2021/1787; G01N 2021/8887;
(Continued)

(56) References Cited

U.S. PATENT DOCUMENTS

| 4,152,069 | A | | 5/1979 | Bruck | |
| 5,811,817 | A | * | 9/1998 | Ravich | ................... G01N 21/87 |
| | | | | | 250/372 |

(Continued)

FOREIGN PATENT DOCUMENTS

| CA | 2618237 A1 | * | 3/2007 |
| DE | 3738041 A1 | * | 12/1988 |

(Continued)

OTHER PUBLICATIONS

International Search Report and Written Opinion for the International Patent Application No. PCT/EP2018/059493, dated Jun. 15, 2018, 12 pages.

*Primary Examiner* — Michael P Stafira
(74) *Attorney, Agent, or Firm* — Kacvinsky Daisak Bluni PLLC

(57) ABSTRACT

A method of analysing an at least partially transparent object, such as a gemstone, includes fixing the object in a holder; immersing the object in the holder in an immersion material; and analysing internal and/or external features of the object. Analysing comprises visualizing an internal and/or external portion of the object using light rays while the object is immersed in the immersion material, and determining characteristics of the object based on the visualized internal and/or external portion of the object. During the analysing step, the difference between the refractive index (RI) of the immersion material and the RI of at least an immersed portion of the holder, which is in contact with the object, is less than 0.3.

23 Claims, 11 Drawing Sheets

(51) Int. Cl.
*G01N 21/41* (2006.01)
*G01N 33/38* (2006.01)

(58) Field of Classification Search
CPC ............... G01N 21/4795; G01N 21/65; G01N 21/8806; G01N 21/8851; G01N 2201/062; G01N 23/046; G01N 2021/8809; G01N 2021/8829; G01N 2021/8848; G01N 2021/8861; G01N 2021/8883; G01N 21/03; G01N 21/41; G01N 21/658; G01N 21/68; G01N 2201/0221; G01N 2201/0231; G01N 2201/025; G01N 2201/06113; G01N 2223/04; G01N 2223/3304; G01N 2223/419; G01N 2223/646; G01N 23/04; G01N 23/041; G01N 23/083; G01N 23/18; G01N 23/20; G01N 23/20008; G01N 23/20016; G01N 23/20025; G01N 23/201; G01N 23/203; G01N 23/205; G01N 23/2055; G01N 23/207; G01N 21/9501; G01N 21/956; G01N 2021/0342; G01N 21/05; G01N 2021/0346; G01N 21/6428; G01N 21/4788; G01N 21/648; G01N 21/21; G01N 21/6458; G01N 21/8507; G01N 2021/6432; G01N 2021/651; G01N 2021/95615; G01N 21/76; G01N 21/8422; G01N 2201/068; G01N 2333/95; G01N 27/44721; G01N 27/44782; G01N 33/551; G01N 33/552; G01N 33/553; G01N 33/573; G01N 15/082; G01N 15/0826; G01N 2015/0873; G01N 2021/0378; G01N 2021/0392; G01N 2021/6478; G01N 2021/6482; G01N 2021/8822; G01N 21/0303; G01N 21/274; G01N 21/3577; G01N 21/552; G01N 21/77; G01N 21/88; G01N 2201/06186; G01N 33/2888; G01N 1/30; G01N 1/42; G01N 1/44; G01N 2021/7789; G01N 21/45; G01N 21/47; G01N 21/63; G01N 21/95; G01N 21/95607; G01N 33/6848; G01N 15/088; G01N 2015/086; G01N 2021/0375; G01N 2021/3595; G01N 2021/451; G01N 2021/6419; G01N 2021/6421; G01N 2021/6439; G01N 2021/6441; G01N 2021/7786; G01N 2021/95676; G01N 21/0332; G01N 21/13; G01N 21/15; G01N 21/359; G01N 21/6408; G01N 21/645; G01N 21/7703; G01N 21/93; G01N 21/94; G01N 30/74; G01N 33/54373; G01N 7/14; G01N 15/00; G01N 15/0205; G01N 15/14; G01N 2015/0065; G01N 2015/0216; G01N 2015/0222; G01N 2015/145; G01N 2021/0325; G01N 2021/0339; G01N 2021/035; G01N 2021/4742; G01N 2021/479; G01N 2021/7783; G01N 2035/00237; G01N 2035/1062; G01N 21/01; G01N 21/17; G01N 21/4133; G01N 21/474; G01N 21/49; G01N 21/53; G01N 21/553; G01N 21/6454; G01N 21/78; G01N 21/82; G01N 21/958; G01N 2201/0627; G01N 2201/0638; G01N 2291/015; G01N 2291/02416; G01N 2291/02466; G01N 2800/122; G01N 29/032; G01N 29/222; G01N 29/348; G01N 3/42; G01N 33/38; G01N 33/386; G01N 33/5044; G01N 33/54393; G01N 35/0099; G02B 1/02; G02B 1/002; G02B 27/0922; G02B 27/0955; G02B 5/0221; G02B 5/0226; G02B 5/0242; G02B 5/0284; G02B 5/0833; G02B 5/1857; G02B 5/26; G02B 5/285; G02B 17/08; G02B 1/06; G02B 1/11; G02B 1/115; G02B 1/12; G02B 26/105; G02B 27/0012; G02B 27/4233; G02B 3/12; G02B 3/14; G02B 5/10; G02B 5/1819; G02B 5/1842; G02B 6/02347; G02B 6/0238; G02B 6/02385; G02B 6/0239; G02B 6/1225; G02B 6/305; G02B 6/32; G02B 6/34; G02B 6/4208; G02B 6/4214; G02B 6/43; G01B 9/02091; G01B 11/005; G01B 11/25; G01B 11/30
See application file for complete search history.

(56) References Cited

U.S. PATENT DOCUMENTS

| | | | | |
|---|---|---|---|---|
| 6,239,867 B1* | 5/2001 | Aggarwal | ............... | G01N 21/87 356/30 |
| 6,980,283 B1 | 12/2005 | Aggarwal | | |
| 7,324,188 B1* | 1/2008 | Beesley | ............... | G01N 21/359 356/30 |
| 2004/0112087 A1 | 6/2004 | Bishop | | |
| 2005/0190356 A1* | 9/2005 | Sasian | ................ | G01N 21/01 356/30 |
| 2006/0196858 A1* | 9/2006 | Barron | ................ | B23K 26/03 219/121.69 |
| 2008/0231833 A1* | 9/2008 | Shlezinger | ............ | G01N 21/15 356/30 |
| 2009/0147241 A1* | 6/2009 | Shlezinger | ............ | G01N 21/87 356/30 |
| 2013/0010280 A1* | 1/2013 | Palmieri | ............... | G01N 21/87 356/30 |
| 2015/0293038 A1* | 10/2015 | Orlov | .................... | G01N 21/87 356/128 |
| 2018/0372647 A1* | 12/2018 | Brenner | ................ | G01N 21/87 |

FOREIGN PATENT DOCUMENTS

| | | | |
|---|---|---|---|
| DE | 3914882 A1 | * | 11/1990 |
| DE | 3914882 A1 | | 11/1990 |
| DE | 102015105944 A1 | * | 10/2016 |
| GB | 2204963 A | | 11/1988 |
| WO | 2012004351 A1 | | 1/2012 |

\* cited by examiner

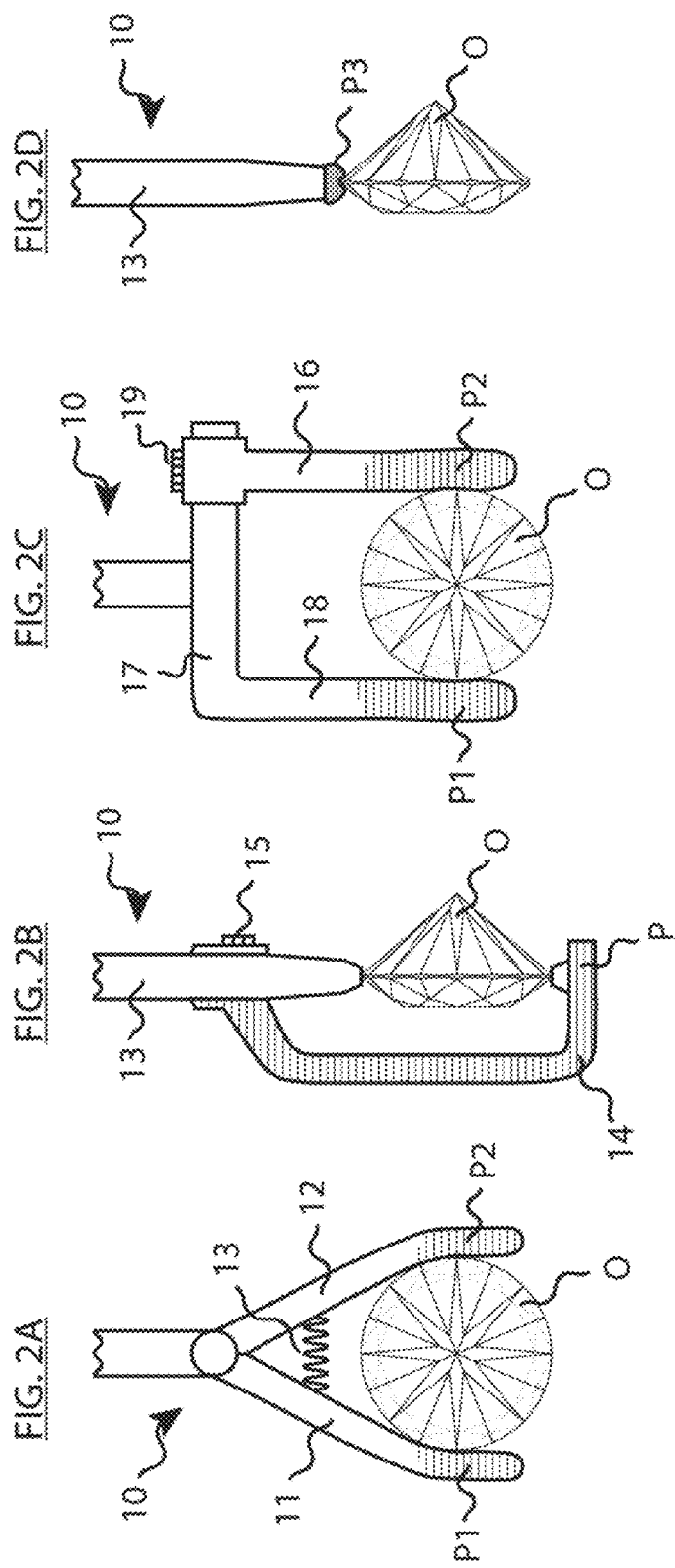

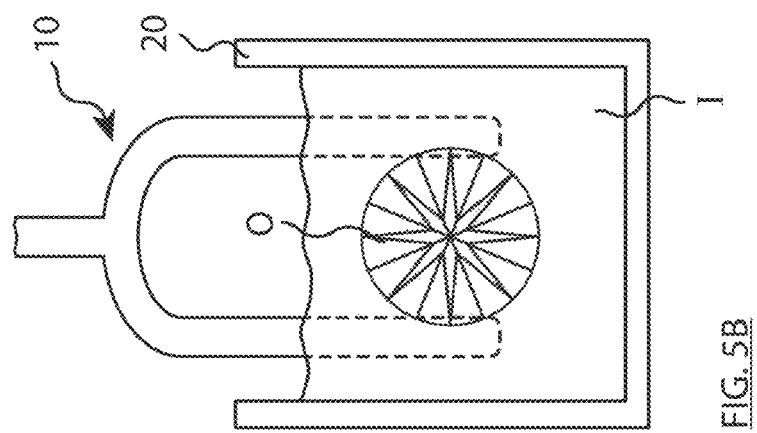
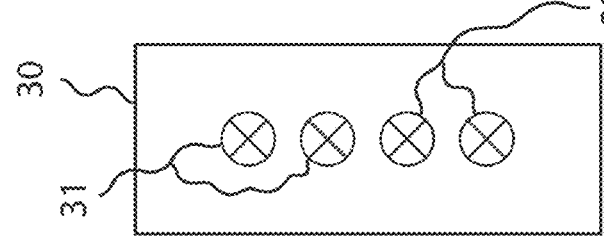
FIG.5B
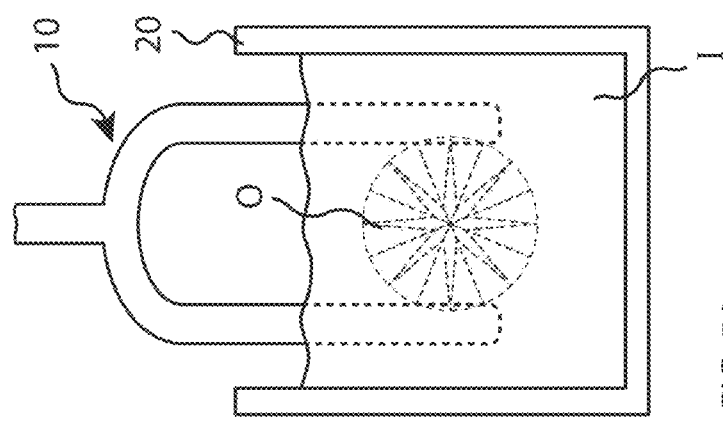
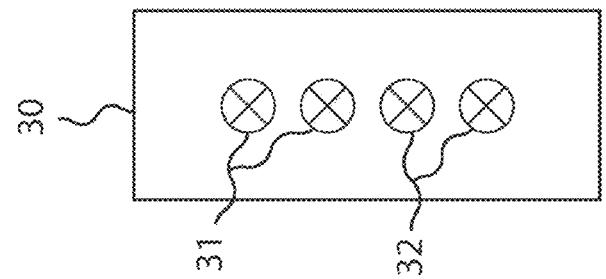
FIG.5A

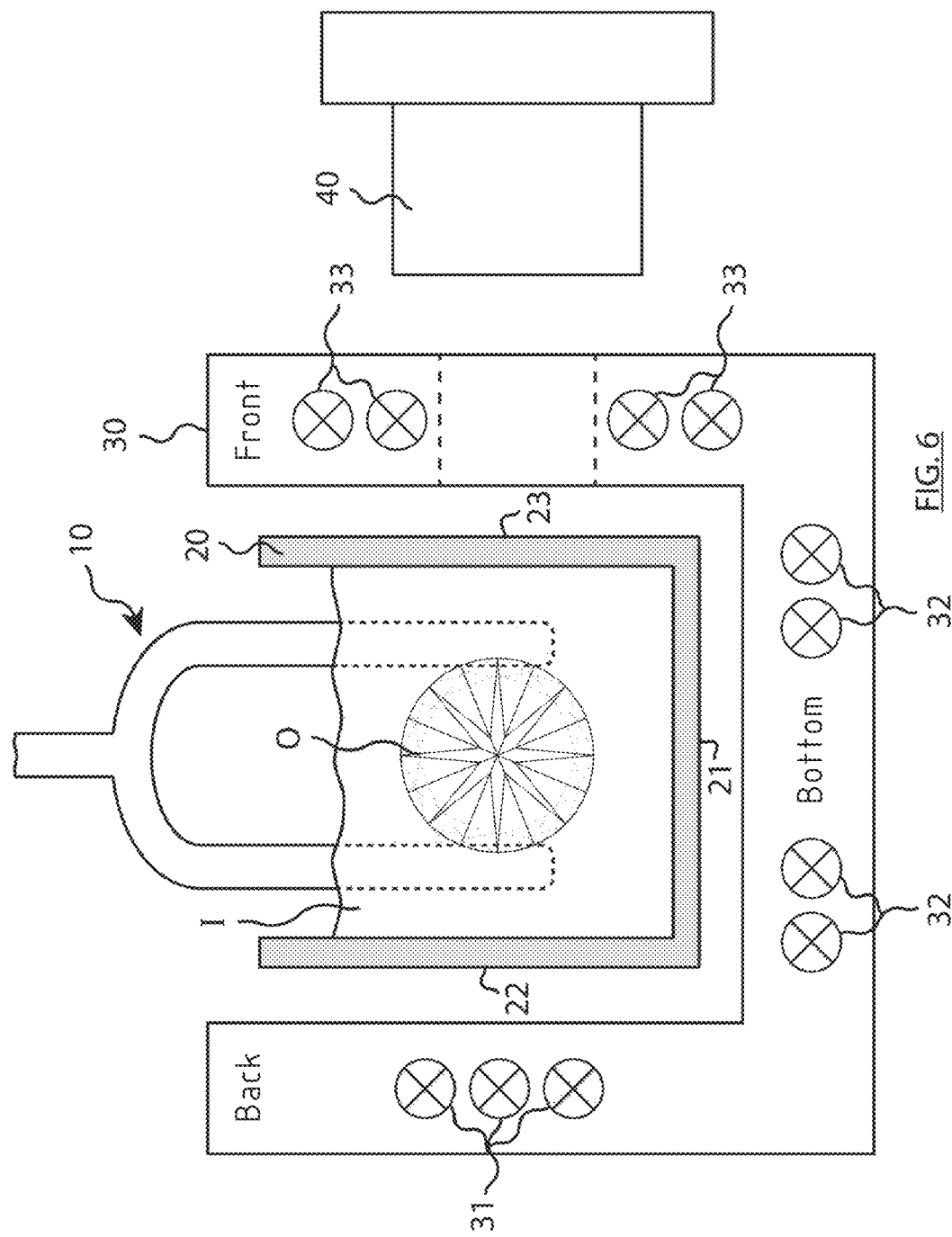

METHOD FOR ANALYSING A GEMSTONE

This is a national stage application filed under 35 U.S.C. § 371 of pending international application PCT/EP2018/059493 filed Apr. 13, 2018, which claims priority to Belgian Patent application BE 20175270, filed Apr. 19, 2017, the entirety of which applications are hereby incorporated by reference herein.

FIELD OF THE INVENTION

The present invention relates to a method and system for analysing an at least partially transparent object, such as a gemstone, and in particular for analysing internal and/or external features of a gemstone, such as inclusions. Embodiments of the invention are described herein with particular reference to evaluation of diamonds, but the skilled person will understand that the invention is also applicable to other types of precious and semi-precious gemstones. Moreover, the invention is applicable for both rough gemstones, polished gemstones as well as semi-polished gemstones. In addition, the invention is also applicable for any at least partially transparent object that requires study of its internal and/or external features, such as objects made of glass and synthetic minerals with different shapes.

BACKGROUND

The value of a cut diamond is determined to a significant extent by the four C's: cut, clarity, carat and colour. In addition to measuring weight, colour, size and cut, to evaluate the diamond, the inclusions must be located and their influence on the cost of the final brilliant must be minimized. The stone may have internal or external flaws or inclusions. Note that the terms "flaw", "inclusion" and "defect" are used as synonyms referring to a visually discernible irregularity inside the gemstone. There are various causes of inclusions, e.g. crystals of a foreign material, another crystal of the gemstone itself, or imperfections such as cracks which may appear whitish or cloudy. The clarity of a gemstone such as a diamond will depend on the number, size, colour, location, orientation and visibility of the inclusions. By locating and identifying inclusions within a rough (unpolished) gemstone, it is possible, in principle, to plan the cutting of the gemstone in such a manner as to minimize the impact of those inclusions upon the clarity of the final cut and polished stone.

The task of evaluating a diamond appears at almost all stages of the process from mining to selling. The choice of the evaluation method in a particular case depends on many factors. From the point of view of technique, many methods have been developed historically. One known method is based on the use of an immersion liquid. In this method, typically, a diamond is glued to a holder and submerged in an immersion solution with the same refractive index as diamond. As a result, the diamond "disappears", but any inclusions remain visible. The stone in the immersion liquid is rotated and 2D images are obtained from a plurality of different viewing directions to determine properties of the inclusion(s). A problem which occurs when using this method is that the holder holding the diamond remains visible during the analysis, and the obscuration or reflection of light caused by the holder hampers the quality of evaluation. In addition, the diamond cannot be evaluated from all directions due the obscuration caused by the holder.

WO2012/004351 in the name of the applicant addresses this problem and discloses a method for analysing a gemstone, typically for locating inclusions in a gemstone, comprising the steps of: selecting a solid material which is transparent in at least a segment of the visible spectrum; melting or plasticizing said solid material and immersing the gemstone in said melted or plasticized material such that the gemstone is at least partly covered therein; allowing said melted or plasticized material to become solid such that a solid transparent block is obtained containing the gemstone; and analysing the gemstone through a surface of the transparent block using light rays in the visible spectrum. By immersing the gemstone in a solid block it is not necessary to polish out windows in the gemstone itself, avoiding the risk that volume of the potential polished stone is decreased. This also means that after examination if the gemstone is under pre-purchase consideration and is rejected based on the inclusion evaluation, the gemstone can be removed from the transparent material and returned to its owner. Although this method addresses the above mentioned problem, it may not always be desirable to include the object to be analysed in a solid block.

SUMMARY OF THE INVENTION

It is an object of embodiments of the present invention to provide an improved method for analysing an at least partially transparent object, such as a gemstone, which allows for obtaining an improved view of the internal and/or external features of the at least partially transparent object without having to built in the object in a solid material.

According to an aspect of the invention there is provided a method for analysing an at least partially transparent object, such as a gemstone, comprising: fixing the object in a holder; immersing the object in the holder in an immersion material; analysing internal and/or external features of the object. The analysing comprises visualizing an internal and/or external portion of the object using light rays of a wavelength while the object is immersed in the immersion material, and determining characteristics of the object based on the visualized internal and/or external portion of the object. Under the conditions at which the analysing is performed, the difference between the refractive index (RI) of the immersion material and the RI of at least an immersed portion of the holder which is in contact with the object is less than 0.3.

By selecting an immersion material that has a RI similar to the RI of the immersed portion of the holder, the holder remains substantially "invisible" during the analysis of the object and in the images obtained. Therefore any obscuration or reflection of light by the holder is significantly reduced, improving the quality of analysis. Indeed, the visualizing of an internal and/or external portion of the object while the object is immersed in the immersion material, will result in images with less "noise" caused by the holder. Hence, the determining of characteristics of the object using computer means based on the visualized internal and/or external portion of the object, will result in improved results.

The conditions comprise any conditions that may influence the value of the refractive index during the analysing, such as the temperature range used during the analysing and the wavelength range used during the analysing. The refractive index of a material is dependent on the temperature and the wavelength of the light rays. Preferably, the immersion material is selected such that for the temperature and wavelength range used during the analysing, the difference between the RI of the object and the RI of the immersion material is lower than 0.3.

Preferably, under the conditions at which the analysing is performed, the difference between the RI of the object and the RI of the immersion material is lower than the difference between the RI of the gemstone and the RI of air. More preferably, the difference between the RI of the object and the RI of the immersion material is less than 0.5, even more preferably less than 0.3. This will further improve the quality of the obtained images.

Preferably, under the conditions at which the analysing is performed, the difference between the RI of the immersion material and the RI of the immersed portion of the holder is less than 0.2, more preferably less than 0.1, and most preferably less than 0.05. However if the RI of the studied object is low enough to match more or less with the RI of the immersion liquid, then the immersed portion of the holder may be made from the same material as studied object.

According to an exemplary embodiment, the visualizing comprises a step of illuminating the object while the object in the holder is immersed in the immersion material, and detecting the illumination having passed through the illuminated object in order to obtain a 2D image. The illuminating may be done using light rays with different wavelengths, e.g. using light rays in the visible spectrum.

Preferably the analysing is controlled by computer means. For example, the moving of the holder, the illuminating by an illumination system and/or the detecting of light having passed though the illuminated object may be controlled by one or more computers. More in particular, the computer means can control the holder, the illumination system, and the detector in order to obtain images of the object in different positions of the holder with respect to the illuminating system and detector.

From those images relevant information regarding the internal and/or external features of the object may be derived. If the object is a gemstone, e.g. a location and/or shape of an inclusion can be derived. More in particular such images will allow building a 3D model of an inclusion of the gemstone. For the building of a 3D model of an inclusion based on images of the gemstone, further reference is made to U.S. Pat. No. 9,292,966 in the name of the same inventor, which is included herein by reference.

According to yet another exemplary embodiment, the at least partially transparent object is a gemstone, such as diamond, ruby, sapphire and emerald. However embodiments of the invention can also be used to analyse any at least partially transparent object that requires study of its internal and/or external features, for example, objects made of glass and synthetic minerals with various shapes, e.g. flat plates, cylinders, lenses, and complex forms.

According to yet another exemplary embodiment, the immersed portion of the holder is made of a material or a combination of materials belonging to the classes of glass, or quartz, or plastic.

Preferably, the immersion material is an immersion liquid, more preferably a transparent or translucent liquid. Preferably, the transmittance of the immersion liquid, under the conditions used during the analysing, is larger than 10%, more preferably larger than 50%, and most preferably larger than 75%. The transmittance depends on the immersion liquid used, the thickness of the liquid layer, the wavelength and the temperature, and the immersion liquid and/or the analysing conditions are preferably chosen such that the transmittance of the immersion liquid, is larger than 10%, more preferably larger than 50%, and most preferably larger than 75%.

Preferably the immersion liquid is an oil. In an exemplary embodiment, under the conditions used during the analysing, the oil has a refractive index between 1.43 and 1.45, e.g. RI approximately 1.44. Oil with RI of approximately 1.44 has the advantage that the RI is close to the RI of fused silica which is a suitable material for manufacturing the holder. In another exemplary embodiment, under the conditions used during the analysing, the oil has a refractive index between 1.51 and 1.53, e.g. RI approximately 1.52. In that case quartz can be used for manufacturing the holder.

According to an exemplary embodiment, the analysing comprises translating and/or rotating the holder, so that the visualizing of the object can be done from a plurality of directions.

According to an exemplary embodiment, the analysing comprises selecting at least one monochromatic light source with a certain wavelength from a plurality of monochromatic light sources with different wavelengths. This will allow optimizing the analysing. For example, when different object features have to be analysed, the analysis of which requires different optimal wavelengths, then this embodiment will allow selecting the post appropriate wavelength for the respective feature to be analysed, resulting in an improved analysis result. Also, the wavelength may be selected such that the difference in RI between the object to be measured and the RI of the immersion material is minimal.

According to an exemplary embodiment, the analysing comprises selecting at least one monochromatic light source set at a certain location from a plurality of monochromatic light sources set at different locations. This will allow optimizing the analysing. For example, using light sources set at different locations, the object can be illuminated from different directions, and different object features can be better revealed.

According to an exemplary embodiment, the analysing comprises controlling the temperature of the immersion material during the analysing in order to control the difference between the RI of the immersion material and the RI of the immersed portion of the holder, and more in particular in order to minimize said difference for the wavelength used. In that manner a close match between the RI of the immersed portion of the holder and the RI of the immersion material can be achieved for a defined monochromatic light source as will be further explained below with reference to FIGS. 8A and 8B.

According another aspect of the invention there is also provided a system for analysing an at least partially transparent object, such as a gemstone, comprising: a holder for fixing the object; a cuvette with an immersion material; and an analysing system configured for analysing internal and/or external features of the object, wherein the analysing comprises visualizing an internal and/or external portion of the object using light rays while the object is immersed in the immersion material, and determining characteristics of the object based on the visualized internal and/or external portion of the object. The immersion material, the holder and the analysing system are configured such that, during the analysing, the difference between the refractive index (RI) of the immersion material and the RI of at least an immersed portion of the holder which is in contact with the object is less than 0.3.

In an exemplary embodiment the analysing system comprises: an illumination system configured to illuminate the object in the holder when immersed in the immersion material; and a detector configured to detect illumination having passed through the illuminated object, such as a camera. The illumination system may comprise a plurality of monochromatic light sources with different wavelengths.

Further, the illumination system may comprise a plurality of monochromatic light sources set at different locations. Preferably, the analysing system comprises a drive means configured for translating and/or rotating the holder, such that the visualizing of the object can be done from a plurality of directions. Preferably, the analysing system comprises a computer means configured for controlling at least one of the drive means, the illumination system, and the detector. The computer means may be a single computer and/or a plurality of computers.

The skilled person understands that the features and considerations disclosed in the above method embodiments apply mutatis mutandis to the system.

Preferably, the immersion material, the holder and the analysing system are configured such that, during the analysing, the difference between the RI of the immersion material and the RI of the immersed portion of the holder is less than 0.2, more preferably less than 0.1, and most preferably less than 0.05.

Preferably the holder is configured for mechanically clamping the object to be analysed. Alternatively or in addition the object may be glued to the holder. Preferably, the glue is semi-transparent and has approximately the same RI as the immersion liquid. Preferably, the difference between the RI of the glue and the RI of the immersion liquid, under the analysing conditions, is smaller than 0.3, more preferably smaller than 0.2. In that manner the object will have substantially no hidden zones.

According to an exemplary embodiment, at least the immersed portion of the holder is made of a material or a combination of materials belonging to the classes of glass, or quartz, or plastic.

Preferably the immersion liquid is an oil, e.g. an oil as specified above in connection with the embodiments of the method.

According to an exemplary embodiment the analysing system comprises a temperature control means configured to control the temperature of the immersion material during the analysing in order to control the difference between the RI of the immersion material and the RI of the immersed portion of the holder, and in particular in order to minimize said difference by controlling the temperature of the immersion liquid for the wavelength used.

BRIEF DESCRIPTION OF THE DRAWINGS

The invention will be further elucidated on the basis of a number of non-limitative exemplary embodiments of the method of the invention, with reference to the accompanying drawings.

FIGS. 2A, 2B, 2C and 2D illustrate different exemplary embodiments of a holder suitable for fixing the object.

FIGS. 5A and 5B illustrate a schematic view of a second exemplary embodiment of the system in accordance with the present invention.

FIG. 6 illustrates a schematic view of a third embodiment of the system in accordance with the present invention.

DETAILED DESCRIPTION OF EMBODIMENTS

Figure 1:
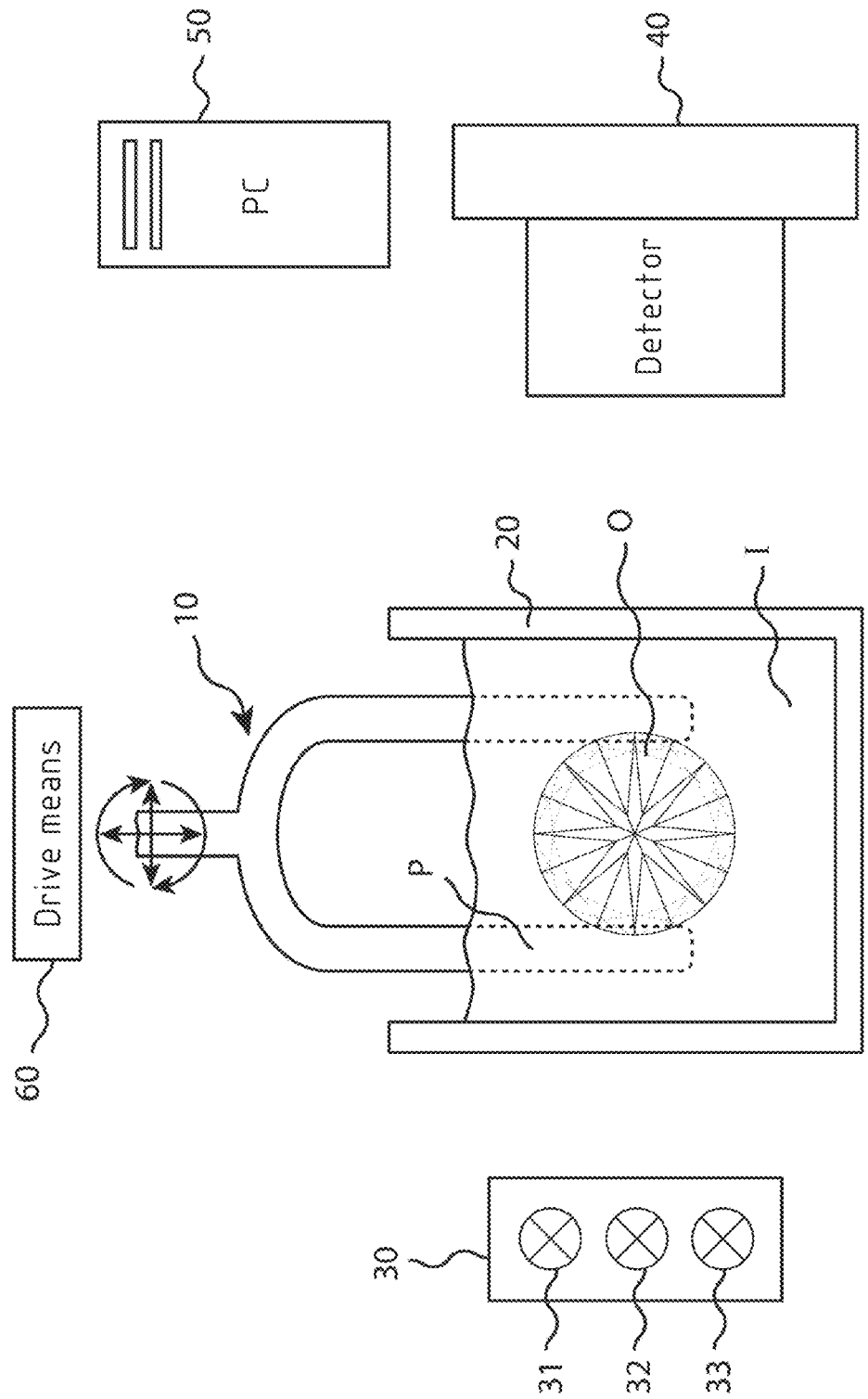
FIG. 1 is a schematic illustration of a system for analysing an at least partially transparent object, such as a gemstone, in accordance with an exemplary embodiment of the invention.

FIG. 1 is a schematic illustration of a system for analysing an at least partially transparent object O in accordance with an exemplary embodiment. In the exemplary embodiment in FIG. 1, the at least partially transparent object O is a gemstone, such as diamond, ruby, sapphire or emerald. However embodiments of the invention can also be used to analyse any at least partially transparent object O that requires study of its internal and/or external features, for example, objects made of glass and synthetic minerals with different shapes, such as flat plates, cylinders, lenses, and objects with a complex shape.

The system of the exemplary embodiment comprises a holder 10 for fixing the object O, a cuvette 20 with an immersion material I, an analysing system comprising an illumination system 30 configured to illuminate the object O in the holder 10 when immersed in the immersion material I, and a detector 40 configured to detect corresponding illumination having passed through the illuminated object O. The detector 40 is for example a camera. The difference between the refractive index (RI) of the immersion material and the RI of the immersed portion of the holder, under conditions used during the analysing of the object, is less than 0.3, preferably less than 0.2, more preferably less than 0.1, and most preferably less than 0.05. Preferably, at least the immersed portion P of the holder 10 is made of a material or a combination of materials belonging to the classes of glass, or quartz, or plastic. Preferably, the immersion liquid I is oil, preferably a lapping oil with an RI between 1.40 and 1.50, under conditions used during the analysing of the object. The cuvette 20 may be made of any material, preferably a transparent or translucent material such as glass or quartz.

The illumination system 30 may comprise a plurality of monochromatic light sources 31, 32, 33. The different light sources 31, 32, 33 may have the same or a different wavelength, and may be positioned at different locations. Preferably, there is provided a first plurality of monochromatic light sources 31 at a first location, said first plurality of light sources having different wavelengths, and a second plurality of monochromatic light sources 32 at a second location, said second plurality of light sources having different wavelengths. Alternatively, there may be provided a first light source 31 capable of emitting light with different wavelengths at a first location, and a second light source 32 capable of emitting light with different wavelengths at a second location. In that manner, a light source of the first plurality may be selected depending on e.g. a feature of the object that is to be analysed. Further, by providing light sources at different positions, the object can be illuminated according to different orientations.

Further, the analysing system comprises a drive means 60 configured for translating and/or rotating the holder. Also the analysing system comprises a computer means 50 configured for controlling the drive means 60, the illumination system 30, and the detector 40.

The holder 10 is shown schematically in FIG. 1, but may be embodied in many different ways. Preferably the holder 10 is configured to mechanically clamp the object 10. FIGS. 2A-2C illustrate three possible embodiments for the holder 10. The holder 10 comprises a mechanism that clamps the object O between two points on the object O, and the holder 10 is preferably configured such that the holder 10 is suitable for holding objects O with different sizes and shapes. For example, FIG. 2A shows schematically a holder 10 with a first arm 11 and a second arm 12 which is mounted pivotally with respect to the first arm 11, and with a spring means 13 mounted between the first arm 11 and the second arm 12 of the holder. At least end portions P1, P2 of the arms 11, 12 of the holder 10 are made of a material with a RI which is similar to the RI of the immersion material I. FIG. 2B shows another embodiment of a holder 10 comprising an upper part 13 and a lower part 14 which is moveable with respect to the upper part 13 such that objects O of variable size can be clamped between the upper part 13 and the lower part 14. The upper and the lower part 13, 14 may be configured such that the lower part 14 can be fixed with respect to the upper part 13, e.g. by a screw 15 in a suitable position for clamping the object O. FIG. 2C shows yet another embodiment of a holder 10 with a first arm 18 and a second arm 16, wherein an object O is clamped between the first arm 18 and the second arm 16. The second arm 16 of the holder 10 is movable along a rigid and fixed guidance part 17 of the holder 10. The second arm 16 may be fixed with respect to guidance part 17 with a fixation means, e.g. a screw 19. Alternatively, as illustrated in FIG. 2D, the object O can be glued onto a holder 10 instead of being clamped. More in particular, the holder 10 may comprise an elongate rod 13 with a bottom end on which the object O is fixed using a glue layer P3. Preferably, under the conditions used during measuring, the difference between the refractive index of the glue and the refractive index of the immersion liquid is smaller than 0.3, more preferably smaller than 0.2, even more preferably smaller than 0.1.

Preferably, the holder 10 is mounted such that it can be translated and/or rotated via drive means 60, in order to reposition the studied object relative to the illumination system 30 and the detector 40, such that the visualizing of the object can be done from a plurality of directions. At least an immersed portion P; P1, P2 of the holder 10 is made of a material or a combination of materials belonging to the classes of glass, or quartz, or plastic. The immersion material I is preferably a substantially transparent liquid. However, according to another embodiment of the invention, the immersion material I can also be a substantially transparent semi-liquid, such as a gel. The immersion material I is selected such that the difference between the refractive index (RI) of the immersion material I and the RI of at least an immersed portion of the holder 10 which is in contact with the object O, under conditions used during the analysing of the object, is less than 0.3, preferably less than 0.2, more preferably less than 0.1, and most preferably less than 0.05. The immersion liquid I may be an oil, preferably a lapping oil. At least the immersed portion of the holder 10 is preferably made of a material belonging to the class of quartz.

An exemplary embodiment of the method will be described with reference to FIG. 1. First the object O is fixed in the holder 10. Next the object O is immersed into the immersion material I in the cuvette 20 and positioned at the right position in the immersion material I in the cuvette 20 using the drive means 60. The next step is to analyse the internal and/or external features of the object O. The object O is first illuminated by the illumination system 30, e.g. by one or more light sources 31, 32, 33. The detector 40 detects the corresponding illumination, e.g. light rays, having passed through the illuminated object O, and visualizes its internal and/or external portion. Typically a 2D image of the illuminated object O is obtained. The object O may be repositioned for at least one time by translating and/or rotating the holder 10 using the drive means 60 controlled by the computer means 50, such that the visualizing of the object O is done from a plurality of directions. Next the characteristics of the object O are determined using computer means 50 based on the visualized internal and/or external portion of the object, i.e. based on the obtained 2D images of the illuminated object O.

Figure 3B:
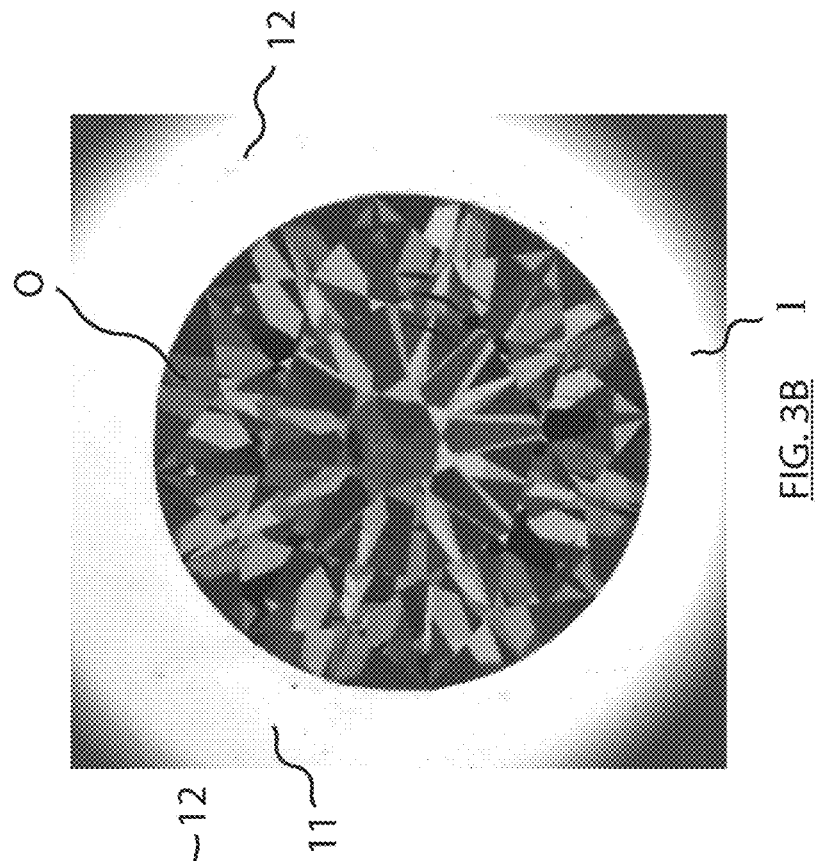
FIGS. 3A and 3B show a first image of a gemstone fixed in a fused silica holder in air and a second image of a gemstone fixed in a fused silica holder immersed in oil, respectively, in a crown view of the gemstone.
Figure 3A:
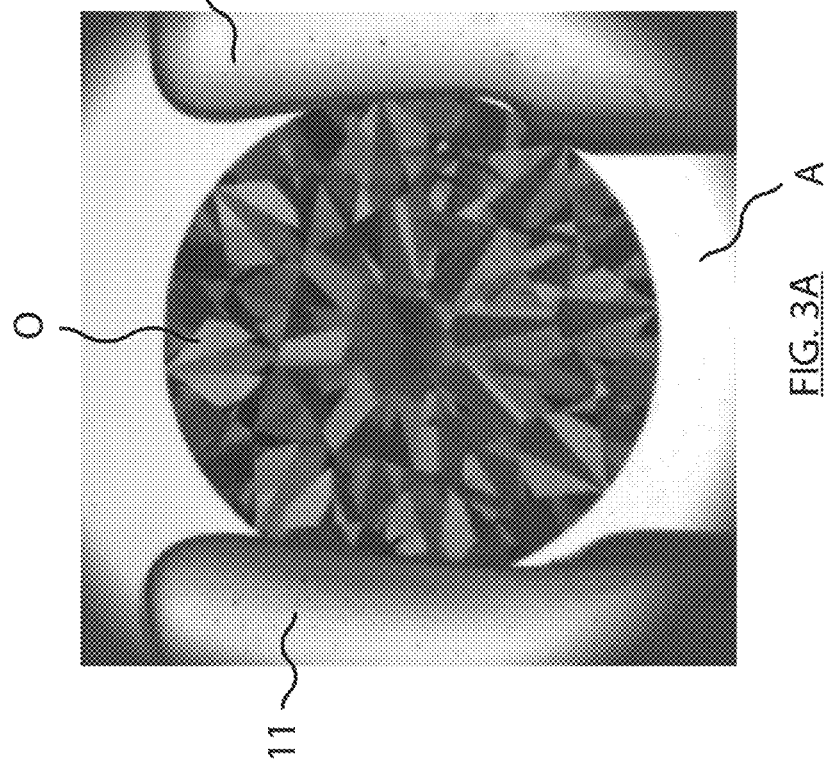

FIGS. 3A and 3B illustrate how the selection of the immersion material I and of the material of the holder 10 influences the obtained image of the object O to be analysed. In the example the object O is a diamond, and the holder 10 has two arms 11, 12 made of glass with a RI of 1.46 under conditions used during the analysing of the object. In FIG. 3A, the diamond O in the glass holder 10 is placed in air A. In view of the large difference between the RI of air A and the RI of the glass holder 10, parts of the diamond O are obscured by reflection of light from the holder 10. However when the diamond O in the glass holder 10 is immersed in an immersion oil with a RI of 1.46 under conditions used during the analysing of the object, as in FIG. 3B, the image generated is substantially free from any obscuration or reflection caused by the holder 10, and the complete diamond area can be observed substantially without "noise" caused by the presence of the holder 10. Moreover, the diamond O can be observed from a complete set of directions without being hindered by obscuration or reflection caused by the holder 10.

Figure 4B:
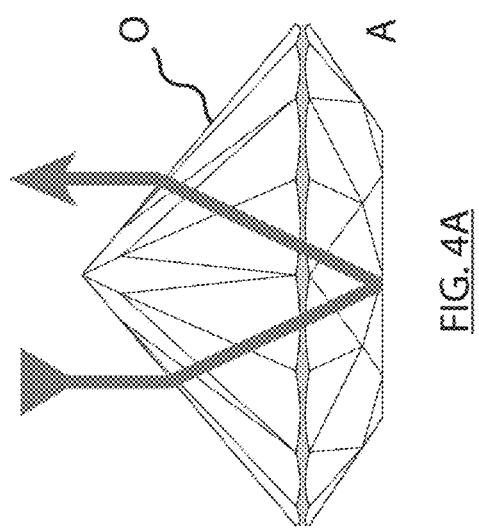
FIGS. 4A and 4B show schematically, in a side view, the light transmission paths in a gemstone, wherein light enters the pavilion side, and wherein the gemstone is fixed in a fused silica holder present in air and in a fused silica holder immersed in oil, respectively.
Figure 4A:
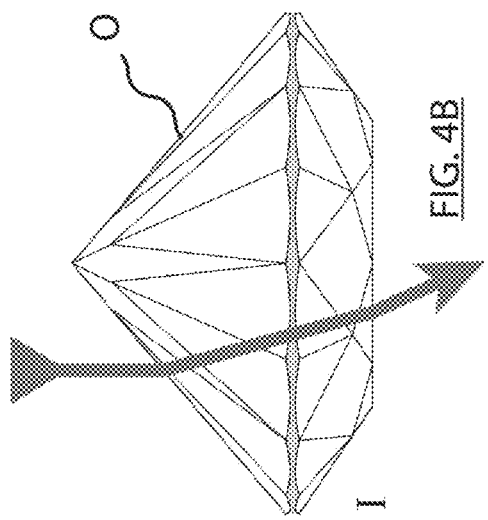
Figure 4D:
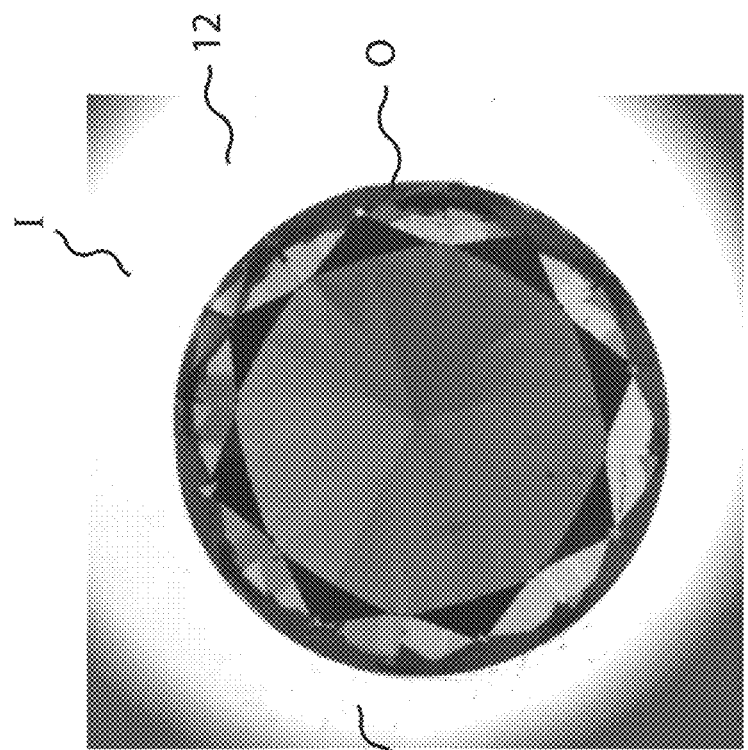
FIGS. 4C and 4D show a first image of a gemstone fixed in a fused silica holder in air and a second image of a gemstone fixed in a fused silica holder immersed in oil, respectively, in a pavilion view of the gemstone.
Figure 4C:
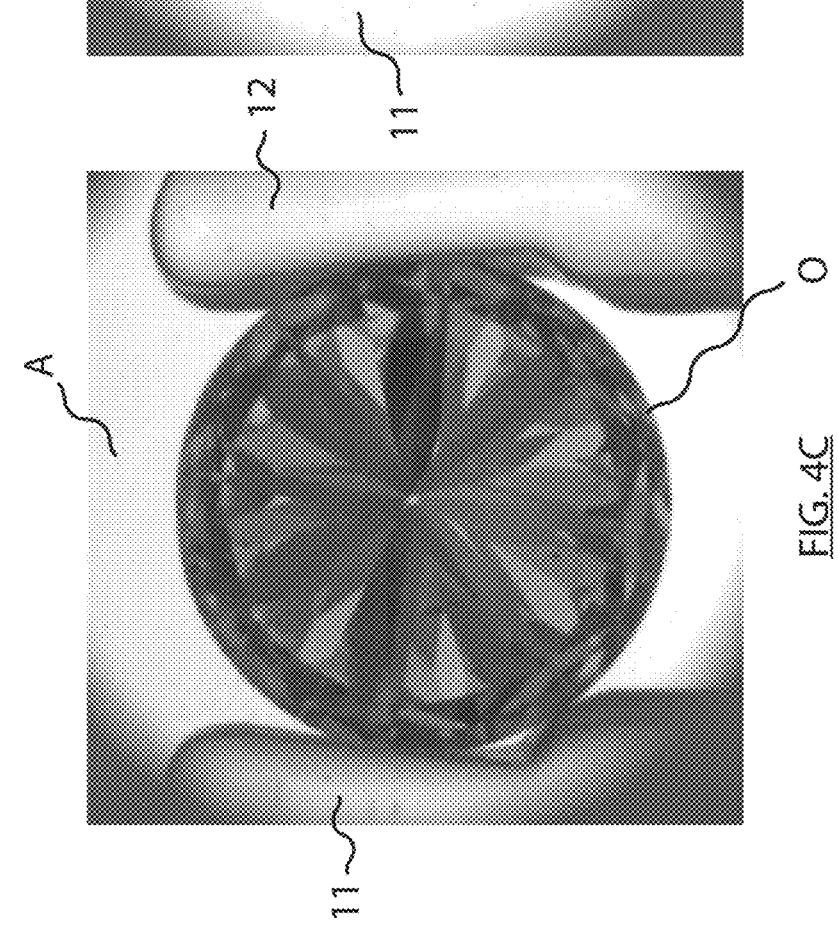

FIGS. 4A to 4D show how exemplary embodiments are useful in obtaining a pavilion view of a gemstone O, such as a diamond. FIGS. 4A and 4B illustrate the paths of light transmission in a diamond O when illuminating the diamond from the pavilion side, and FIGS. 4C and 4D illustrate the pavilion views of the diamond, using a glass holder 10 in air A or in the immersion oil I respectively, as is in FIGS. 3A and 3B. When viewed from pavilion using a glass holder 10 in air A, significant reflections are generated at the interface between the diamond O and the air A when the light ray is exiting the gemstone O (FIG. 4A). As a result, multiple pavilion reflections from different facets of the diamond can be observed (FIG. 4C). When using an exemplary embodiment of the present invention, there is more light transmission at the interface between the diamond O and the immersion oil I for light rays exiting the diamond O (FIG. 4B). As a result, a clear window and an improved viewing area for observing internal features is obtained (FIG. 4D).

FIGS. 5A and 5B show another exemplary embodiment of a system. In this embodiment the illumination system 30 comprises monochromatic light sources 31, 32 with different wavelengths. In such an embodiment the analysing of the object O may comprise selecting at least one monochromatic light source 31 with a certain wavelength from a plurality of monochromatic light sources 31, 32 with different wavelengths. As the RI of a material is a function of the wavelength, the wavelength may be selected in function of e.g. the material of the object O and/or the immersion material and/or the material of the immersed portion of the holder. In that manner the difference in RI between e.g. the immersion material and the material of the immersed portion of the holder may be minimized. It is further possible to select a wavelength in function of the object features to be analysed. For instance in FIG. 5A, a monochromatic light source 31 with a certain wavelength is selected based on minimum RI difference between the immersion material I and the holder 10, for the purpose of generating a high contrast image of the gemstone. On the contrary in FIG. 5B, a monochromatic light source 32 of a different wavelength is selected based on maximum RI difference between the immersion material I and the object O. This may be useful for the purpose of building a 3D model of the object or matching the pre-build 3D model of the object with its real position, for example when analysing objects with a RI close to the RI of the immersion material, of which no visible borders can be observed using monochromatic light source 31.

FIG. 6 shows another exemplary embodiment. In this embodiment, the illumination system 30 comprises monochromatic light sources 31, 32, 33 set at different locations around the cuvette 20. The cuvette 20 has a flat bottom surface 21, and a first and second flat side surface 22, 23 perpendicular on the bottom surface 21. The illumination system 30 comprises a first light source 32 emitting light in the direction of the bottom surface 21, a second light source 31 emitting light in the direction of the first side surface 22, and a third light source 33 emitting light in the direction of the second side surface 23. Optionally further light sources may be provided at a front side and/or a back side and/or at a top side of the cuvette 20 (not shown). In that manner, the immersed object O can be illuminated from different directions. The light sources 31, 32, 33 from different directions can also be switched-on or switched-off in function of the desired illumination. The analysing of the object O comprises selecting at least one monochromatic light source 31 or 32 or 33 set at a certain location from a plurality of monochromatic light sources 31, 32, 33 set at different locations. In a first step the selection may be based on the desired object feature to be observed. If certain object features are best visible using light sources oriented in certain directions, then those features may be analysed using these light sources. Other object features could be analysed using other light sources, which are better visible using those other light sources. The selection may also be based on the position of the object.

Figure 7A:
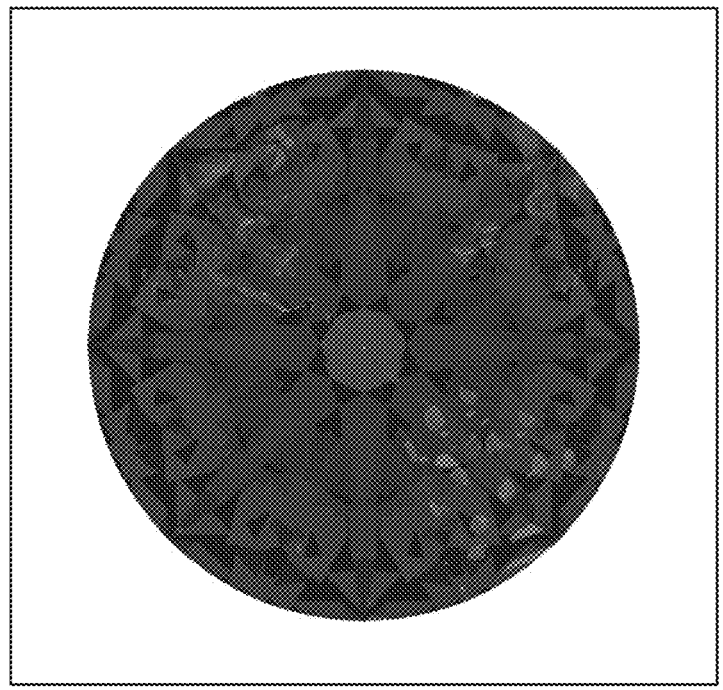
FIGS. 7A and 7B show a first and a second image of a crown view and a pavilion view of a gemstone fixed in a fused silica holder immersed in oil, respectively, using brightfield lighting.
Figure 7B:
Figure 7C:
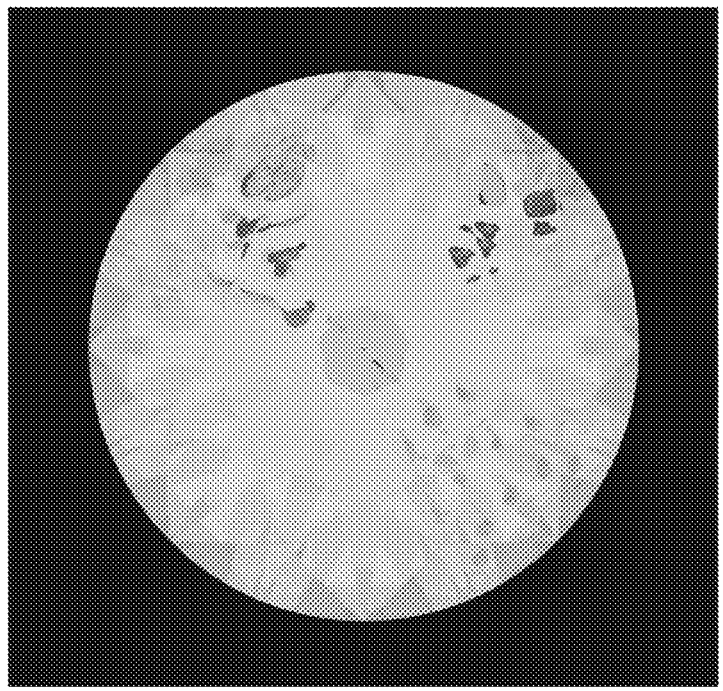
FIGS. 7C and 7D show a first and a second image of a crown view and a pavilion view of a gemstone fixed in a fused silica holder immersed in oil, respectively, using top lighting.
Figure 7D:
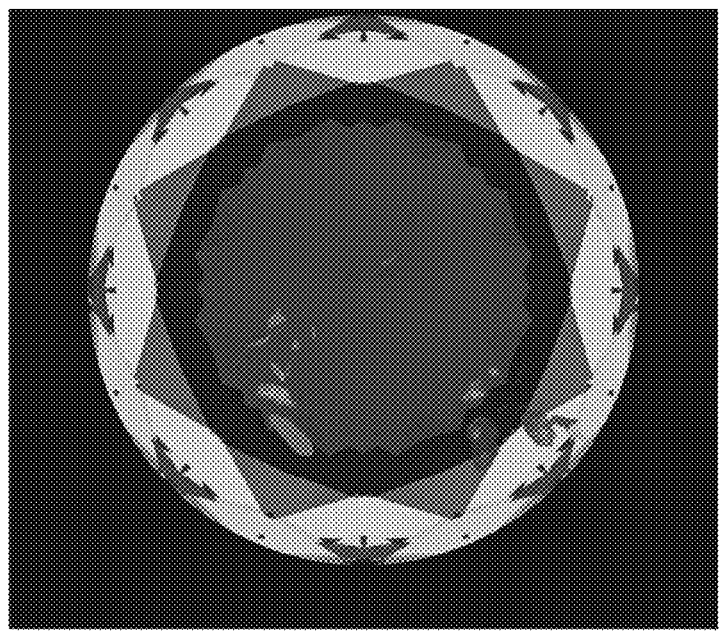

FIGS. 7A-7D illustrate images obtained using an exemplary embodiment of the method. For example in FIGS. 7A-7D, the purpose of a user is to create maximum contrast for the internal features of the object, here a diamond, such as inclusions. For obtaining a pavilion view, preferably a brightfield lighting is selected, as it creates a high contrast image for the inclusions, see FIG. 7B. As shown in FIG. 7D, a top lighting does not result in such a high contrast image. However, when viewing a diamond in a crown view, a top lighting is preferably selected, see FIG. 7C, as it creates a high contrast image for the inclusions, while a brightfield lighting does not result in such a high contrast image for the inclusions, see FIG. 7A.

As explained above, the measurements may be performed with light having different wavelengths and the measurements may be performed at different temperatures. Hence, for specific measurements the difference in RI may be smaller or bigger depending on the wavelength of the light used and depending on the temperature.

In an exemplary embodiment, if it is necessary to perfectly match the RI between the immersion liquid and the holder, and if a light source with the required wavelength is not available, then it is possible to use the light source with nearest wavelength and to adjust the temperature of the immersion liquid and/or the holder to fine tune the RI match between the immersion liquid and the holder.

Figure 8A:
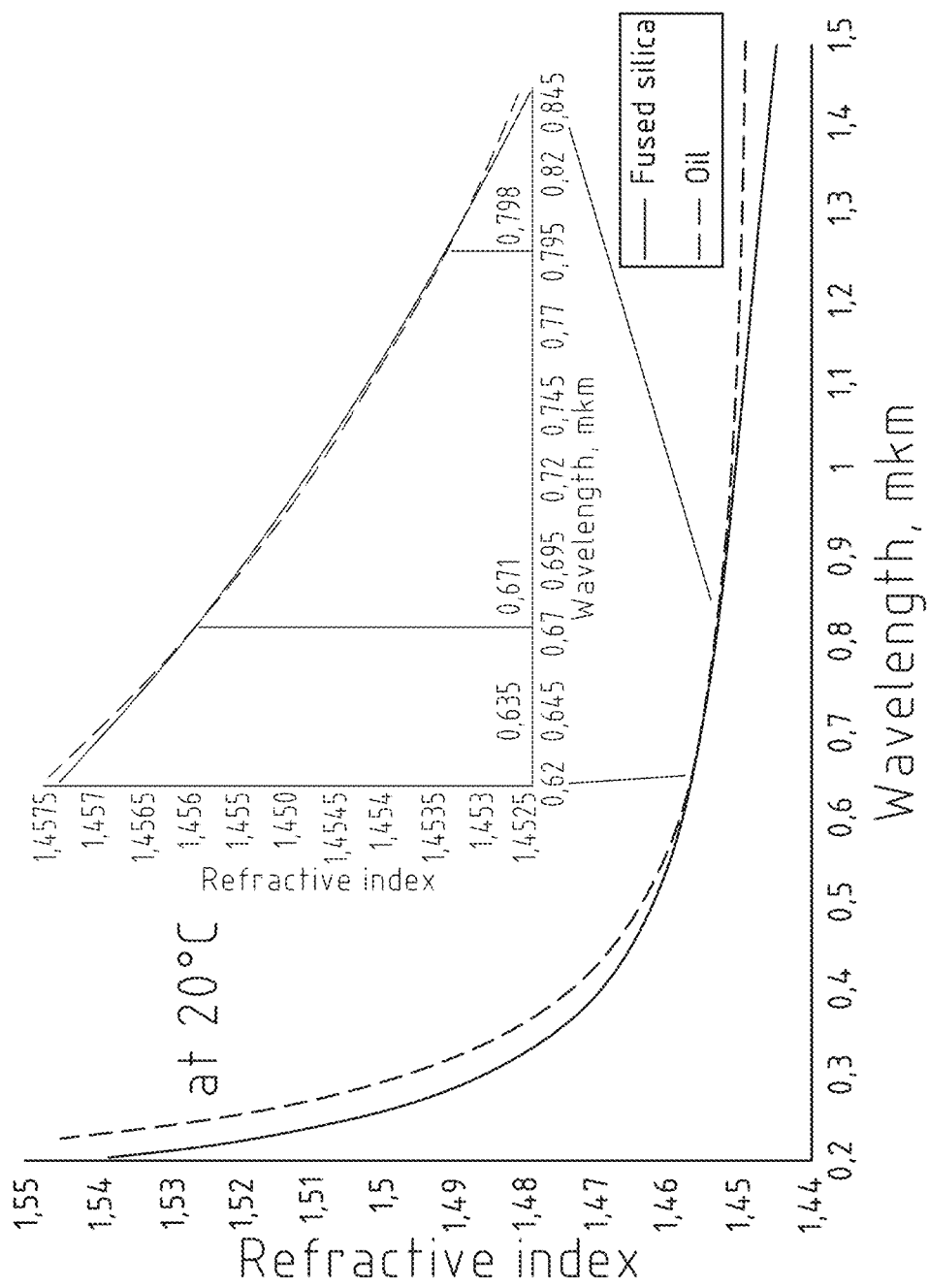
FIGS. 8A and 8B shows a graph of the variation of the refraction indexes of oil and fused silica in function of the light source wavelength and the ambient temperature, respectively.

FIG. 8A shows the RI dependence from light source wavelength for fused silica and oil. For a wavelength in a range of 600-800 nm the RI for fused silica and oil nearly matches. But in UV/blue and near infra-red parts of the spectrum fused silica and oil have a different RI.

Figure 8B:
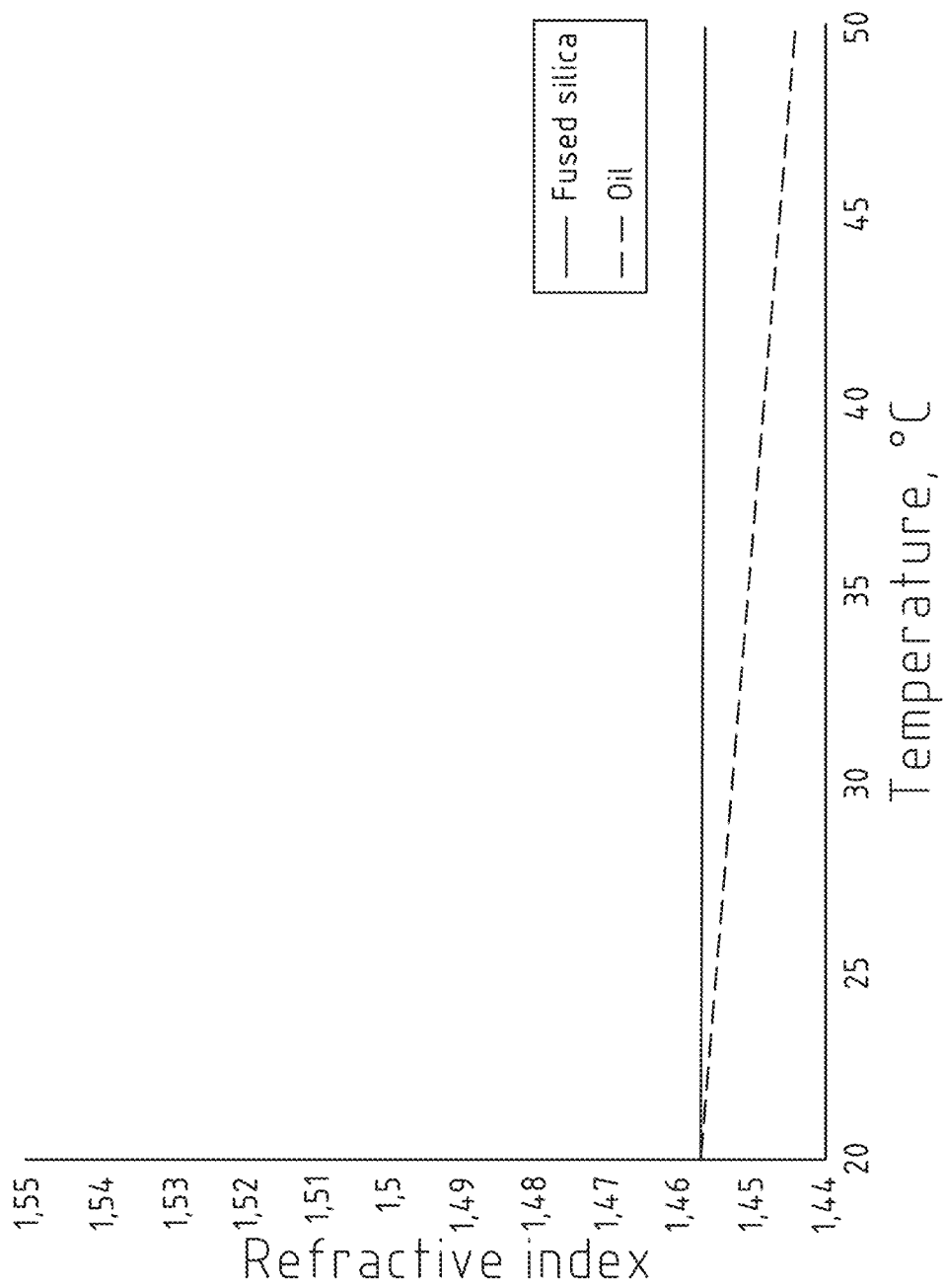

FIG. 8B shows the RI dependence from ambient temperature for fused silica and oil at a wavelength of 600 nm. At 20° C. (and a light wavelength of 600 nm) the RI for fused silica and oil matches. But when temperature increases the RI difference between fused silica also increases. So by adjusting the temperature it is possible to change the RI difference between the oil and holder material at a given wavelength.

It will be understood that the foregoing described embodiments of the invention are intended to be exemplary only, and should not be considered limiting of the scope of the invention, as defined in the following claims.

The invention claimed is:

1. A method of analysing an at least partially transparent object, such as a gemstone, comprising:
   providing a cuvette with an immersion material;
   fixing the object in a holder;
   arranging the holder in the cuvette containing the immersion material such that the object and at least a portion of the holder is immersed in the immersion material; and
   analysing at least one of internal and external features of the object, wherein analysing comprises visualizing at least one of internal and external portion of the object using light rays while the object is immersed in the immersion material, and determining characteristics of the object based on the at least one of visualized internal and external portion of the object;
   wherein, during the analysing, the difference between the refractive index (RI) of the immersion material and the RI of at least an immersed portion of the holder which is in contact with the object, is less than 0.2.

2. The method according to claim 1, wherein, during the analysing, the difference between the RI of the immersion material and the RI of the immersed portion of the holder is less than 0.1.

3. The method according to claim 1, wherein the analysing comprises illuminating the object while the object in the holder is immersed in the immersion material, and detecting the illumination having passed through the illuminated object.

4. The method according to claim 1, wherein the analysing is controlled by computer means.

5. The method according to claim 1, wherein the at least partially transparent object is a gemstone.

6. The method according to claim 1, wherein the immersed portion of the holder is made of a material or a combination of materials belonging to the classes of glass, or quartz, or plastic.

7. The method according to claim 1, wherein the immersion material is a transparent or translucent liquid.

8. The method according to claim 1, wherein the immersion liquid is oil.

9. The method according to claim 1, wherein said analysing comprises at least one of translating and rotating the holder, such that the visualizing of the object is done from a plurality of directions.

10. The method according to claim 1, wherein the analysing comprises selecting at least one monochromatic light source with a certain wavelength from a plurality of monochromatic light sources with different wavelengths.

11. The method according to claim 1, wherein the analysing comprises selecting at least one monochromatic light source set at a certain location from a plurality of monochromatic light sources set at different locations.

12. The method according to claim 1, wherein the analysing comprises controlling the temperature of the immersion material during the analysing so that the difference between the RI of the immersion material and the RI of the immersed portion of the holder is minimized.

13. A system for analysing an at least partially transparent object, such as a gemstone, comprising:
    a holder for fixing the object;
    a cuvette with an immersion material configured to receive the object fixed with the holder and at least a portion of the holder with the object fixed therein; and
    an analysing system configured for analysing at least one of internal and external features of the object, wherein analysing comprises visualizing at least one of an internal and external portion of the object using light rays while the object is immersed in the immersion material, and determining characteristics of the object based on at least one of the visualized internal and external portion of the object;
    wherein the holder, the immersion material and the analysing system are configured such that, during the analysing, the difference between the refractive index (RI) of the immersion material and the RI of at least an immersed portion of the holder which is in contact with the object is less than 0.2.

14. The system according to claim 13, wherein the holder, the immersion material and the analysing system are configured such that, during the analysing, the difference between the RI of the immersion material and the RI of the immersed portion of the holder is less than 0.1.

15. The system according to claim 13, wherein the analysing system comprises: an illumination system configured to illuminate the object in the holder when immersed in the immersion material; and a detector configured to detect illumination having passed through the illuminated object.

16. The system according to claim 15, wherein the illumination system comprises a plurality of monochromatic light sources with different wavelengths, wherein the plurality of light sources comprise one or more of: ultraviolet, visible, near infra-red and infra-red light sources.

17. The system according to claim 15, wherein the illumination system comprises a plurality of monochromatic light sources set at different locations, wherein the analysing system is configured to select at least one monochromatic light source from the plurality of monochromatic light sources.

18. The system according to claim 17, wherein the cuvette has a flat bottom surface, and a first and second flat side surface perpendicular on the bottom surface, wherein the illumination system comprises a first light source emitting light in the direction of the bottom surface, a second light source emitting light in the direction of the first side surface, and a third light source emitting light in the direction of the second side surface.

19. The system according to claim 13, wherein the analysing system comprises a drive means configured for at least one of translating and rotating the holder.

20. The system according to claim 13, wherein at least the immersed portion of the holder is made of a material or a combination of materials belonging to the classes of glass, or quartz, or plastic.

21. The system according to claim 13, wherein the holder is configured to mechanically clamp the object.

22. The system according to claim 13, wherein the analysing system comprises a temperature control means configured to control the temperature of the immersion material during the analysing so that the difference between the RI of the immersion material and the RI of the immersed portion of the holder is minimized.

23. The method according to claim 1, wherein one of the following combinations is used:
    a. the immersed portion of the holder is made of fused silica and the immersion liquid is oil having a refractive index between 1.43 and 1.45;
    b. the immersed portion of the holder is made of quartz and the immersion liquid is oil having a refractive index between 1.51 and 1.53 or the immersion liquid is a lapping oil.

* * * * *